US009962180B2

(12) United States Patent
Steele

(10) Patent No.: US 9,962,180 B2
(45) Date of Patent: May 8, 2018

(54) CATHETER INCLUDING DRIVE ASSEMBLY FOR ROTATING AND RECIPROCATING TISSUE-REMOVING ELEMENT

(71) Applicant: Covidien LP, Mansfield, MA (US)

(72) Inventor: Bradley Steele, Plymouth, MN (US)

(73) Assignee: Covidien LP, Mansfield, MA (US)

( * ) Notice: Subject to any disclaimer, the term of this patent is extended or adjusted under 35 U.S.C. 154(b) by 80 days.

(21) Appl. No.: 15/139,459

(22) Filed: Apr. 27, 2016

(65) Prior Publication Data
US 2017/0311968 A1 Nov. 2, 2017

(51) Int. Cl.
| | |
|---|---|
| *A61B 17/22* | (2006.01) |
| *A61D 1/02* | (2006.01) |
| *A61B 17/32* | (2006.01) |
| *A61B 17/3207* | (2006.01) |

(52) U.S. Cl.
CPC ............ *A61B 17/32002* (2013.01); *A61B 17/320758* (2013.01); *A61B 17/320783* (2013.01); *A61B 2017/320028* (2013.01); *A61B 2017/320032* (2013.01); *A61B 2017/320791* (2013.01)

(58) Field of Classification Search
CPC ........ A61B 17/3207; A61B 17/320758; A61B 17/320783; A61B 17/32002; A61B 2017/320024; A61B 2017/320028; A61B 2017/320032; A61B 2017/320741; A61B 2017/320791
USPC .......................................... 606/159, 167, 180
See application file for complete search history.

(56) References Cited

U.S. PATENT DOCUMENTS

| | | | |
|---|---|---|---|
| 4,210,146 | A | 7/1980 | Banko |
| 4,781,181 | A | 11/1988 | Tanguy |
| 4,994,067 | A | 2/1991 | Summers |
| 5,133,725 | A | 7/1992 | Quadri |
| 5,224,949 | A | 7/1993 | Gomringer et al. |
| 5,490,860 | A | 2/1996 | Middle et al. |

(Continued)

FOREIGN PATENT DOCUMENTS

| | | |
|---|---|---|
| EP | 0286415 A2 | 10/1988 |
| EP | 1 595 503 A2 | 11/2005 |

(Continued)

OTHER PUBLICATIONS

PCT/US2017/026666, The International Search Report and the Written Opinion of the International Searching Authority, dated Aug. 14, 2017, 12 pgs.

*Primary Examiner* — Melanie Tyson

(57) ABSTRACT

A tissue-removing catheter includes a drive assembly operatively connected to a drive shaft to impart rotation and reciprocation to the drive shaft and thereby rotate and reciprocate a tissue-removing element of the catheter. The drive assembly includes a prime mover configured to generate a rotational drive force and a reciprocating rotor operatively connected to the prime mover to receive the rotational drive force. The rotor is also operatively connected to the drive shaft to impart rotation and reciprocation to the drive shaft. The drive assembly can include a stator configured to constrain rotation and reciprocation of the reciprocating rotor relative to an axis of the rotor. The rotor can define a race that extends around the rotor axis, and the stator can define one or more bearing projections that track through the race as the prime mover rotates the rotor about the rotor axis to drive reciprocation of the rotor.

29 Claims, 8 Drawing Sheets

(56) References Cited

U.S. PATENT DOCUMENTS

| | | | |
|---|---|---|---|
| 5,507,795 A | 4/1996 | Chiang et al. | |
| 5,632,754 A | 5/1997 | Farley et al. | |
| 5,899,915 A | 5/1999 | Saadat | |
| 6,299,622 B1 | 10/2001 | Snow et al. | |
| 6,623,496 B2 | 9/2003 | Snow et al. | |
| D480,807 S | 10/2003 | Yardan et al. | |
| 6,830,545 B2 | 12/2004 | Bendall | |
| 7,018,390 B2 | 3/2006 | Turovskiy et al. | |
| 7,223,230 B2 | 5/2007 | Zirps et al. | |
| 7,326,224 B2 | 2/2008 | Houde et al. | |
| 7,708,749 B2 | 5/2010 | Simpson et al. | |
| 7,789,825 B2 | 9/2010 | Nobis et al. | |
| 7,862,518 B2 | 1/2011 | Parihar | |
| 8,128,647 B2 | 3/2012 | Kennedy | |
| 8,241,315 B2 | 8/2012 | Jenson et al. | |
| 8,496,677 B2 | 7/2013 | Zhang et al. | |
| 2003/0018346 A1 | 1/2003 | Follmer et al. | |
| 2003/0083684 A1* | 5/2003 | Cesarini | A61B 17/32002 606/170 |
| 2003/0125757 A1 | 7/2003 | Patel et al. | |
| 2005/0222663 A1 | 10/2005 | Simpson et al. | |
| 2006/0276749 A1 | 12/2006 | Selmon et al. | |
| 2007/0016071 A1 | 1/2007 | Eberle et al. | |
| 2008/0004643 A1 | 1/2008 | To et al. | |
| 2008/0140101 A1 | 6/2008 | Carley et al. | |
| 2009/0187203 A1 | 7/2009 | Corvi et al. | |
| 2009/0270897 A1 | 10/2009 | Adams et al. | |
| 2010/0130850 A1 | 5/2010 | Pakter | |
| 2011/0130777 A1 | 6/2011 | Zhang et al. | |
| 2011/0144673 A1 | 6/2011 | Zhang et al. | |
| 2011/0166575 A1 | 7/2011 | Assell et al. | |
| 2011/0270256 A1 | 11/2011 | Nelson et al. | |
| 2011/0306995 A1 | 12/2011 | Moberg | |
| 2014/0031844 A1 | 1/2014 | Kusleika | |
| 2014/0371718 A1 | 12/2014 | Alvarez et al. | |
| 2015/0150578 A1 | 6/2015 | Cesarini et al. | |

FOREIGN PATENT DOCUMENTS

| | | |
|---|---|---|
| FR | 2606267 A1 | 5/1988 |
| SU | 623557 A1 | 9/1978 |
| WO | 03/037194 A1 | 5/2003 |
| WO | 2006/011970 A1 | 2/2006 |
| WO | 2006/105244 A2 | 10/2006 |
| WO | 2007/130711 A1 | 11/2007 |
| WO | 2010/045226 A2 | 4/2010 |
| WO | 2010/132748 A1 | 11/2010 |
| WO | 2011/112918 A2 | 9/2011 |
| WO | 2011/159697 A1 | 12/2011 |
| WO | 2012/003430 A2 | 1/2012 |

* cited by examiner

CATHETER INCLUDING DRIVE ASSEMBLY FOR ROTATING AND RECIPROCATING TISSUE-REMOVING ELEMENT

FIELD

The present disclosure generally relates to a tissue-removing catheter including a drive assembly configured to impart rotation and reciprocation to a tissue-removing element of the catheter.

BACKGROUND

Debulking or tissue-removing catheters are used to remove unwanted tissue from the body. As an example, atherectomy catheters are used to remove material from a blood vessel to open the blood vessel and improve blood flow through the vessel.

SUMMARY

In one aspect, a tissue-removing catheter includes a drive assembly operatively connected to a drive shaft to impart rotation and reciprocation to the drive shaft and thereby rotate and reciprocate a tissue-removing element of the catheter. The drive assembly includes a prime mover configured to generate a rotational drive force and a reciprocating rotor operatively connected to the prime mover to receive the rotational drive force. The rotor is also operatively connected to the drive shaft to impart rotation and reciprocation to the drive shaft. The drive assembly can include a stator configured to constrain rotation and reciprocation of the reciprocating rotor relative to an axis of the rotor. The rotor can define a race that extends around the rotor axis, and the stator can define one or more bearing projections that track through the race as the prime mover rotates the rotor about the rotor axis to drive reciprocation of the rotor.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Embodiments of a tissue-removing catheter having a drive assembly for driving a tissue-removing element of the catheter in simultaneous rotation and oscillation relative to an axis are disclosed. Certain illustrated catheter embodiments are particularly suitable for removing (e.g., excising) plaque tissue from a blood vessel (e.g., peripheral arterial or peripheral venous wall). Other illustrated catheter embodiments are suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from, and penetrating occlusions in, blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Figure 1:
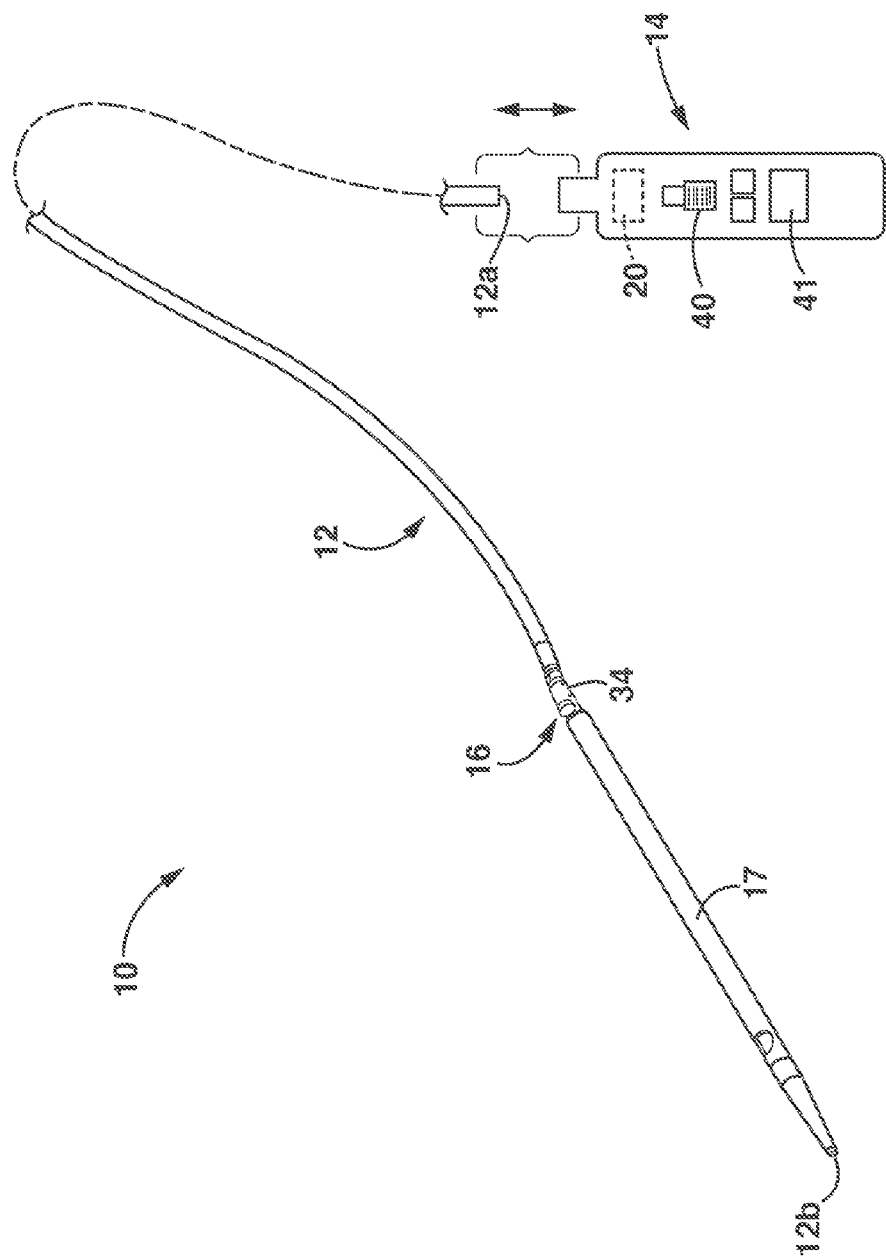
FIG. 1 is a perspective of a catheter body and a schematic representation of a handle, each of which are part of a catheter.

Referring to FIG. 1, a tissue-removing catheter, in accordance with one or more embodiments of the present disclosure, is generally indicated at reference numeral 10. The catheter 10 comprises an elongate catheter body, generally indicated at 12, having opposite proximal and distal ends 12a, 12b, respectively, and a longitudinal axis LA (FIG. 3) extending between the proximal and distal ends. A handle or control unit, generally indicated at 14, is attachable to the proximal end 12a of the catheter body 12, although the handle may be fixedly attached to the catheter body in other embodiments. A tissue-removing element, generally indicated at 16, is located generally adjacent the distal end 12b of the catheter body 12. In the illustrated embodiment, the tissue-removing element 16 comprises a cutting element that is configured to remove (e.g., cut) tissue from the body lumen. The illustrated cutting element 16 is also configured to direct the removed tissue into a tissue container 17. As will be explained in further detail below, the cutting element 16 is operatively connected to a drive assembly 20 in the handle 14 that is suitable for driving the tissue-removing element in simultaneous rotation and oscillation about an axis of rotation RA (FIG. 2) to enhance tissue-removal.

Figure 2:
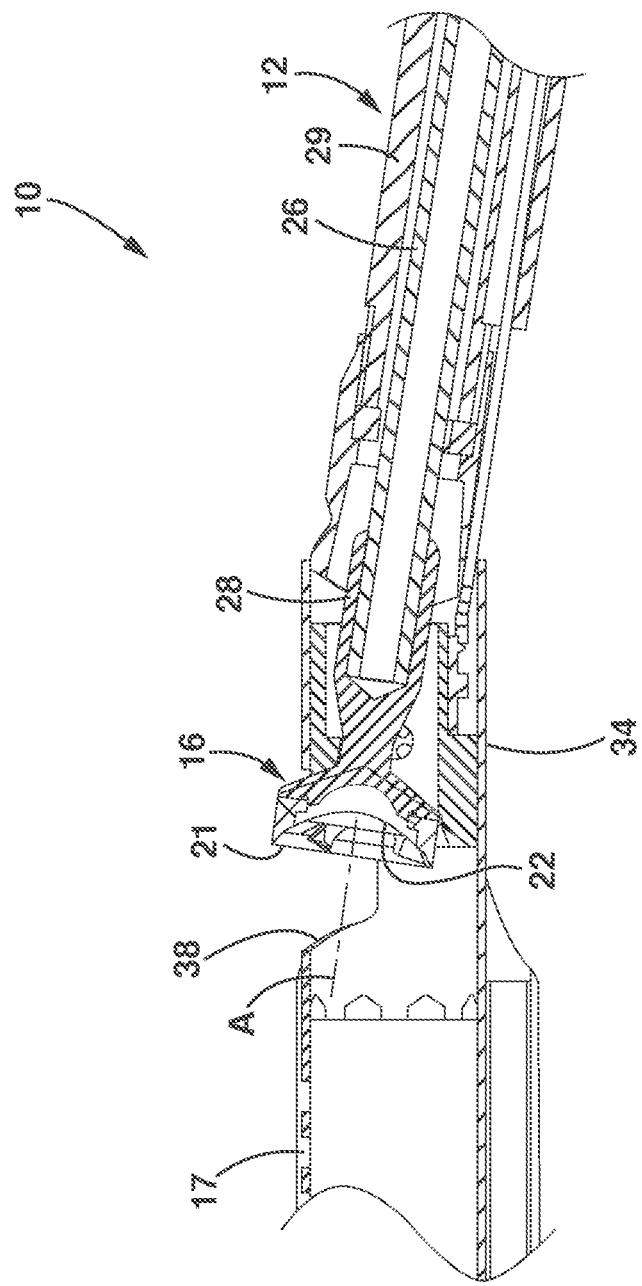
FIG. 2 is an enlarged fragmentary sectional view of the catheter body illustrating a tissue-removing element in a deployed position.
Figure 3:
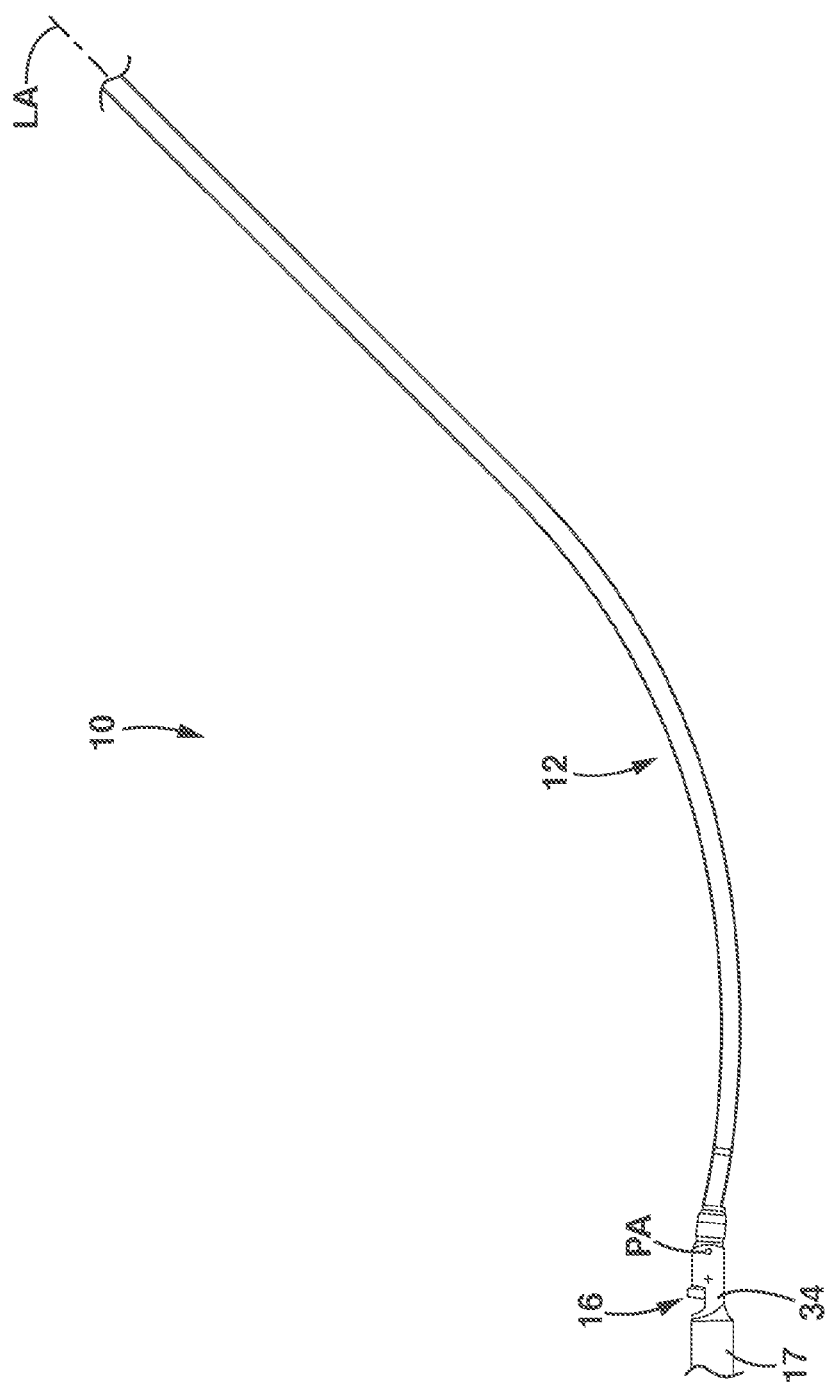
FIG. 3 is an enlarged fragmentary side elevation of the catheter body.

Referring to FIG. 2, in the illustrated embodiment, the cutting element 16 is rotatable about a rotation axis A for cutting tissue. The illustrated cutting element 16 has a cutting edge 21 facing distally and extending circumferentially around the rotation axis A, and a cup-shaped surface 22 for directing removed tissue distally into the tissue container 17 of the catheter body 12. In other embodiments, the tissue-removing element may have other configurations for cutting tissue (e.g., the cutting edge may face proximally, the cutting edge may be located at the distal tip of the catheter as discussed below, etc.), or may be configured to remove tissue in other ways (e.g., the tissue-removing element may be configured to ablate tissue, or abrade tissue, or otherwise remove tissue from the body lumen).

Referring still to FIG. 2, a tissue-removing driveshaft 26 (broadly, a catheter shaft) is operatively connected to a stem 28 of the cutting element 16 (e.g., fixedly secured thereto) and operatively connected to the drive assembly 20 to transmit rotational and reciprocating motion from the drive assembly to the tissue-removing element, as explained in more detail below. The tissue-removing driveshaft 26 (e.g., a coiled or helical driveshaft) extends through a jacket or sheath 29 of the catheter body 12 and is operatively connectable to the drive assembly 20 in the handle 14. The drive shaft 26 is configured for movement relative to the jacket 29. As explained in further detail below, the drive assembly 20 is configured to simultaneously drive rotation and reciprocation of the drive shaft 26 relative to the longitudinal axis LA with respect to the jacket 29.

In addition, as shown in FIG. 1, the drive shaft 26 is operatively connected to a deployment lever or actuator 40 configured to selectively move the drive shaft 26 longitudinally of the catheter body 12 to move the cutting element 16 between the stowed position (not shown) and the deployed position (FIG. 2). In the stowed position, the cutting element 16 is generally disposed in a tissue-removing housing 34 of the catheter body 12 to minimize the cross-sectional size of the catheter body. This allows the catheter body 12 to pass more easily through the blood vessel during insertion. In the deployed position, the cutting element 16 extends radially through a cutting window 38 located adjacent the distal end 12b of the catheter body 12. To deploy the cutting element 16, the driveshaft 26 is moved proximally relative to the catheter body 12, such as by moving the actuator 40 to impart proximal movement of the cutting element 16 relative to the housing 34. As is known in the art, camming engagement between the cutting element 16 and a portion of the housing 34 causes the housing to pivot about a pivot axis PA (FIG. 3), which causes the tissue-removing element to extend partially out of the window 38. To return the cutting element 16 to its stored, non-deployed position, the driveshaft 26 is moved distally using the actuator 40, which causes the housing 34 to pivot or deflect back about the pivot axis PA so that the cutting element is received in the housing 34 in the stowed position. It is understood that a catheter 10 constructed according to the principles of the present disclosure may include other types of deployment mechanisms or may not include a deployment mechanism (e.g., the tissue-removing element or other functional element may always be deployed or may remain within the catheter body). For example, the cutting element 16 or other tissue-removing element may be exposed through the distal end of the catheter body.

In the deployed position, a portion of the cutting element 16 is exposed to engage tissue in a body lumen defined by a blood vessel. As explained in further detail below, with the cutting element 16 deployed, the drive assembly 20 simultaneously imparts rotation and reciprocation of the drive shaft 26 relative to the longitudinal axis LA to drive a cutting action of the cutting element 16. The cutting element 16 simultaneously rotates about the axis of rotation A and reciprocates along the axis of rotation (broadly, rotates and reciprocates relative to the axis of rotation), in response to the rotation and reciprocation of the drive shaft 26, to remove tissue from the body lumen. The rotational motion of the cutting element 16 causes the cutting element to cut or slice through the tissue. The reciprocating motion of the cutting element 16 creates a hammer-like action that is thought to aid in severing hard and soft tissue from the luminal wall by shearing or fracturing the tissue away from the luminal wall. Thus together, the rotation and reciprocating of the cutting element 16 effectively remove tissue from the body lumen by separating tissue from the blood vessel as the catheter 10 advances axially through the body lumen and the drive assembly 20 drives the cutting action of the cutting element.

Figure 4:
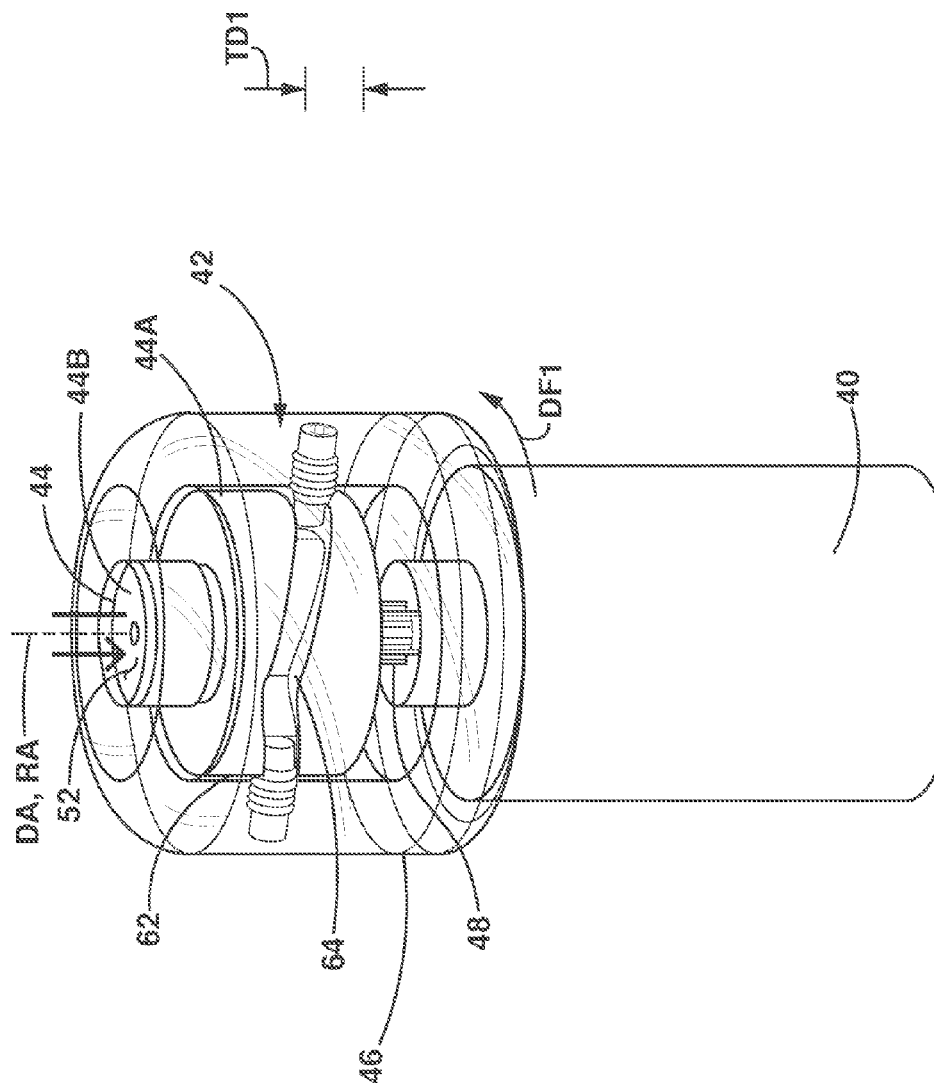
FIG. 4 is a perspective of a drive assembly of the catheter, with a stator of the drive assembly illustrated as a transparent component to reveal a rotor housed within the stator.

Referring to FIG. 4, the illustrated drive assembly 20 is suitable for imparting simultaneous rotation and reciprocation upon the drive shaft 26 to drive the cutting action of the cutting element 18. The drive assembly 20 includes a motor 40 (or other prime mover) that is configured to generate a rotational drive force DF1. In the illustrated embodiment, the drive force DF1 is oriented about a drive axis DA1. But as discussed below, in other embodiments the drive force can be oriented about an axis that is offset from the drive axis. In the illustrated embodiment, the motor 40 is an electrically powered motor that is operatively coupled to a power source such as a battery (not shown). Suitably, the motor 40 can be selectively operable using a switch or other actuator 41 on the handle 14 (FIG. 1). Other embodiments can use other types of motors (e.g., air-driven motors, etc.) or other types of prime movers (e.g., manual rotational input devices) to generate the drive force. The motor 40 is operatively connected to a bearing mechanism, generally indicated at 42, of the drive assembly, which can also be categorized as a cam mechanism. As explained in further detail below, the illustrated bearing mechanism 42 includes a reciprocating rotor 44 mounted on a stator 46 for rotation and reciprocation with respect to the stator. An output shaft 48 (FIG. 5) is coupled to the motor 40 and is mated with the rotor 44 to transmit the drive force DF1 to the rotor. As explained below, the output shaft 48 is shaped and arranged to mate with the reciprocating rotor 44 so that the output shaft imparts rotation of the rotor about a rotor axis RA, and the rotor is movable along the length of the output shaft a throw distance TD1 to allow reciprocating motion of the rotor along the rotor axis.

Figure 5:
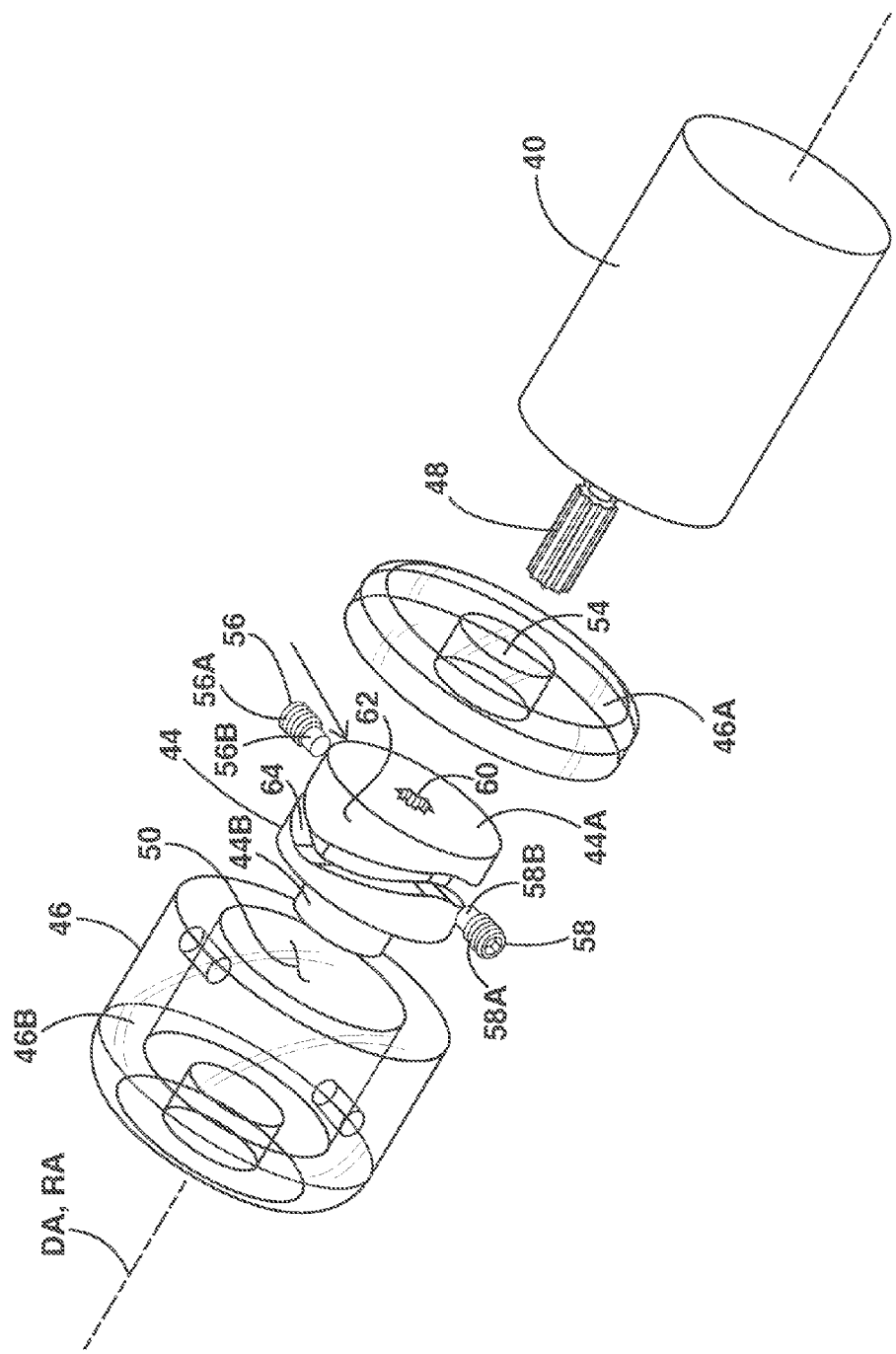
FIG. 5 is an exploded perspective of the drive assembly.
Figure 6:
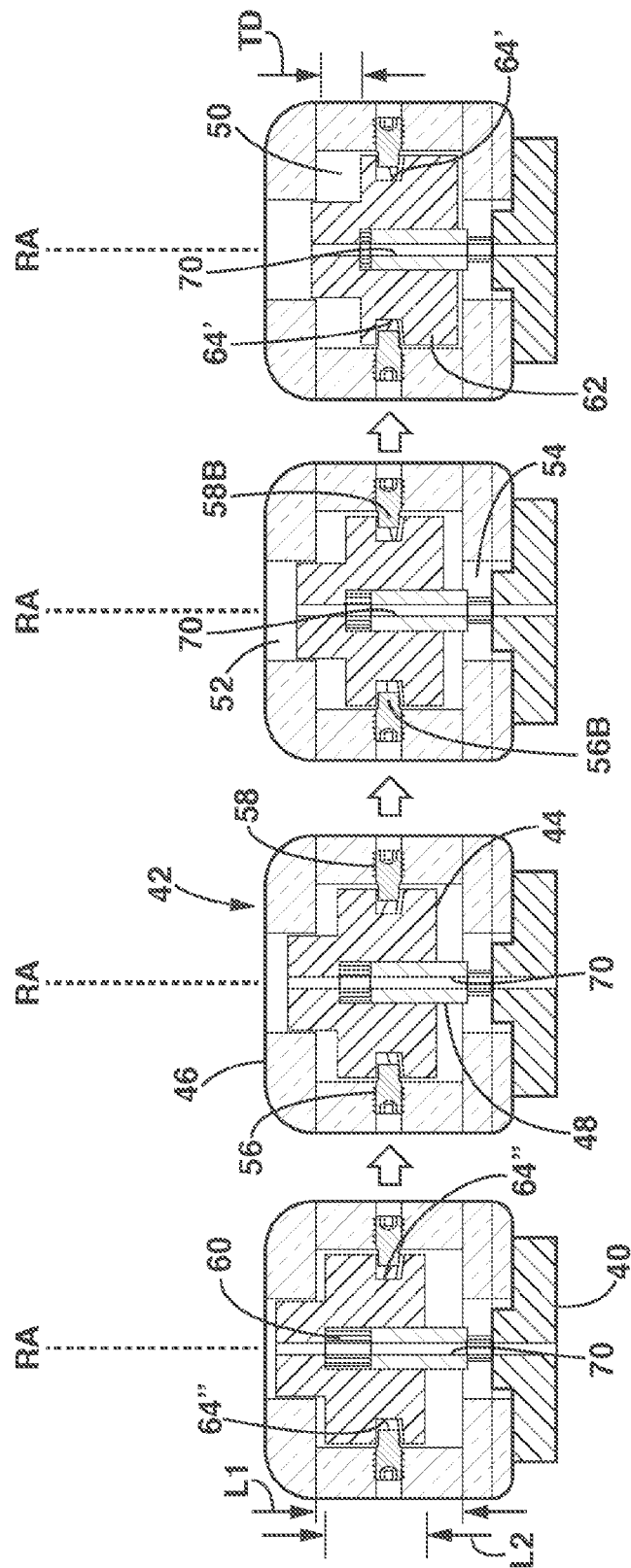
FIG. 6A is fragmentary sectional view of the drive assembly illustrating the rotor at first rotational and axial positions with respect to the stator.
FIG. 6B is fragmentary sectional view of the drive assembly illustrating the rotor at second rotational and axial positions with respect to the stator.
FIG. 6C is fragmentary sectional view of the drive assembly illustrating the rotor at third rotational and axial positions with respect to the stator.
FIG. 6D is fragmentary sectional view of the drive assembly illustrating the rotor at fourth rotational and axial positions with respect to the stator.

Referring to FIG. 5, the stator 46 extends generally along the drive axis DA1 and forms a housing that defines a cavity 50 in which the rotor 44 is received. In operation, the stator 46 is generally fixed in place with respect to the motor 40 and the rotor 44 moves (rotates and reciprocates) relative to the stator and the motor as explained below. In the illustrated embodiment, the stator 46 includes a proximal housing part 46A that defines a proximal wall of the stator extending transverse to the rotor axis RA, and a distal housing part 46B that is attachable to the proximal housing part. The distal housing part 46B defines an axially extending annular wall that extends circumferentially around the rotor axis RA and defines the rotor cavity 50. A smaller diameter distal opening 52 (FIG. 4) extends axially through the distal end wall in communication and generally concentric with the rotor cavity 50. As discussed in further detail below, a portion of the rotor 44 extends into the smaller diameter opening 52 for operative connection with the drive shaft 26 of the catheter 10. A smaller diameter proximal opening 54 (FIG. 4) extends axially through the proximal housing part 46A in communication and generally concentric with the rotor cavity 50. The proximal opening 54 allows passage of the output shaft 48 into the stator housing for mating engagement with the rotor 44, as discussed below. When the proximal housing part 46A is attached to the distal housing part 46B, the cavity 50 is shaped and arranged for receiving the rotor 44 therein to allow the rotor to both rotate within the cavity about the rotor axis RA and reciprocate within the cavity along the rotor axis over the throw distance TD. Although the rotor 44 is received in the stator 46 in the illustrated embodiment, in other embodiments the rotor can define a cavity that receives a portion of the stator therein.

The stator 46 further includes first and second bearing projections 56, 58 (that is, at least one bearing projection) configured to constrain movement of the reciprocating rotor 44 relative to the rotor axis RA (e.g., rotation and reciprocation). Each of the bearing projection 56, 58 includes a threaded portion 56A, 58A and a non-threaded portion 56B, 58B. The threaded portions 56A, 58A comprise pins configured to be threaded into the annular wall of the stator 46 so that the non-threaded portions 56B, 58B extend radially inward from the annular wall into the cavity 50. As explained in further detail below, the bearing projections 56B, 58B are configured to bear against the rotor 44 as the rotor moves relative the stator 46 to guide movement of the rotor relative to the stator. The bearing projections 56, 58 are suitably arranged in diametrically opposed relationship about the rotor axis RA. The bearing projections 56, 58 are axially aligned along the rotor axis RA. Although the illustrated embodiment uses two radially extending bearing projections 56B, 58B, other embodiments can include other numbers of radially extending bearing projections (e.g., one or more bearing projections). Also, the bearing projections may be of other designs and constructions. Furthermore, when in other embodiments the stator is received in a cavity of the rotor, the bearing projections may extend radially outward of the stator instead of radially inward as shown in the illustrated embodiment.

Referring to FIGS. 6A-6D, the rotor 44 is mated with the output shaft 48 to rotate conjointly with the output shaft about the rotor axis RA as the output shaft conveys the drive force RD1 to the rotor, while also permitting the rotor to reciprocate relative to the output shaft along the rotor axis. In the illustrated embodiment, the output shaft 48 comprises a plurality radially extending splines spaced apart circumferentially around the drive axis DA1. The reciprocating rotor 44 includes a socket 60 that extends axially from a proximal end of the rotor. The socket 60 defines axially extending grooves (e.g., internal splines) arranged for engagement with the splines of the output shaft 48 for transferring rotation from the output shaft to the rotor. As illustrated in FIG. 6, the socket 60 is configured to allow axial travel of the output shaft 48 within the socket (e.g., along a travel length that is greater than or equal to the throw distance TD). This allows the rotor 44 to reciprocate relative to the drive shaft 48 as it rotates about the rotor axis RA. As can be understood, the rotor 44 is directly connected to the motor 40 as a direct drive.

Referring again to FIG. 5, the rotor 44 is operatively mounted on the stator 46 for rotation and reciprocation relative to the rotor axis RA with respect to the stator. The rotor 44 defines a race 64 (e.g., a groove) extending around the rotor axis on an exterior, circumferential surface of the rotor. The race 64 operatively receives each of the bearing projections 56B, 58B therein. When the output shaft 48 imparts the drive force DF1 on the rotor 44, the rotor rotates relative to the stator 46 about the rotor axis RA. As the rotor 44 rotates, the bearing projections 56B, 58B travel around (e.g., slide within) the race 64. Sidewalls of the rotor 44 partially defining the race 64 engage the bearing projections 56B, 58B as the bearing projections travel around the race. Thus, the race 64 is sized and shaped to allow tracking of the bearing projections 56B, 58B therein to impart reciprocation of the rotor 44 along the rotor axis RA as the rotor rotates relative to the stator 46.

In the illustrated embodiment, the race 64 extends along an axially sinuous path about the rotor axis RA. As the race 64 extends circumferentially around the rotor axis RA, the race runs distally and then proximally in a periodic fashion. The race 64 suitably has diametric symmetry such that the axial positions of any two diametrically opposed locations along the race are aligned along the rotor axis RA. In the illustrated embodiment, the sinuous path of the race 64 includes first and second distal apexes 64' that are diametrically spaced apart from one another about the rotor axis RA. FIG. 6(D) shows the position of the rotor 44 relative to the stator 46 when the bearing projections 56B, 58B are received in the race 64 at the distal apexes 64'. The sinuous path of the race 64 also includes first and second proximal end points 64" that are diametrically spaced apart from one another about the rotor axis RA. FIG. 6(A) shows the position of the rotor 44 relative to the stator 46 when the bearing projections 56B, 58B are received in the race 64 at the proximal end points 64". The distal apexes 64' and the proximal end points 64" of the race 64 are spaced apart from one another along the rotor axis RA by the throw distance TD.

As can be seen in FIGS. 6(A)-6(B), in one complete rotation of the rotor 44 about the rotor axis RA, the bearing projections 56B, 58B track within the race 64 such that from the proximal end points 64A" (FIG. 6(A)) of the race 64, the bearing projections enter the distal apexes 64A' (FIG. 6(D)) of the race. The bearing projections 56B, 58B then sequentially enter the opposite proximal end points (180° from FIG. 6(A)), and then the opposite distal apexes (180° from FIG. 6(D)). Finally, the bearing projections 56B, 58B enter the proximal end points 64A" (FIG. 6(A)) of the race 64, which is the original position (FIG. 6(A)). Thus, during one complete rotation of the rotor 44 about the rotor axis RA, the rotor completes two reciprocations having the same throw distance TD.

Although the illustrated race 64 is configured to reciprocate the rotor 44 two times for every one rotation, it will be understood that the race can have other shapes to facilitate other ratios of reciprocations-to-rotations. For example, in one embodiment, the race may include first, second, third, and fourth distal apexes, and first, second, third, and fourth proximal end points that are circumferentially spaced apart about the rotor axis RA. This race configuration reciprocates the rotor four times during every complete rotation. Such an embodiment could be arranged for use with a stator comprising four circumferentially spaced apart bearing projections to aid in balancing the rotor on the stator. Still other sinuous groove paths may also be used. Furthermore, in some embodiments, the groove path is not sinuous, but rather is helical, so that the rotor reciprocates once every one, two, or more rotations. Though the race 64 is formed in the exterior surface of the rotor 44 in the illustrated embodiment, in other embodiments the stator can include an axially sinuous groove extending circumferentially around the rotor axis and the rotor can comprise radially extending bearing projections operatively received in the race.

In an exemplary use of the illustrated catheter 10, the user inserts the catheter body 12 into a body lumen and positions the cutting element 16 adjacent a lesion or other tissue formation. The user then deploys the cutting element 16 by drawing the drive shaft 26 proximally of the catheter body 12 using the actuator 40. With the cutting element 16 deployed and in the desired position, the user actuates the switch 41 to activate the motor 40. The motor 40 imparts the drive force DF1 on the output shaft 48, which rotates the rotor 44 relative to the stator 46 about the rotor axis RA. As the rotor 44 rotates, the bearing projections 56B, 58B travel around the race 64 and bear against rotor within the race to reciprocate the rotor along the rotor axis (and relative to the stator). The rotating and reciprocating rotor 44 imparts rotation and reciprocation to the drive shaft 26, causing it to rotate and oscillate relative to its longitudinal axis LA with respect to the catheter jacket 29. The rotating and reciprocating drive shaft 26, in turn, imparts rotation and reciprocation to the deployed cutting element 16, causing it to rotate and reciprocate relative to its axis of rotation A with respect to the catheter body 12. As the cutting element 16 rotates, the edge or blade 21 cuts through tissue in the body lumen. The reciprocation of the cutting element 16 causes the sharp cutting edge 21 to repeatedly impact the tissue, which is thought to shear and/or fracture the cut tissue, thereby severing it from the luminal wall. In the illustrated embodiment, the cup-shaped surface 22 directs the severed tissue into the tissue container 17 for subsequent disposal.

Figure 7:
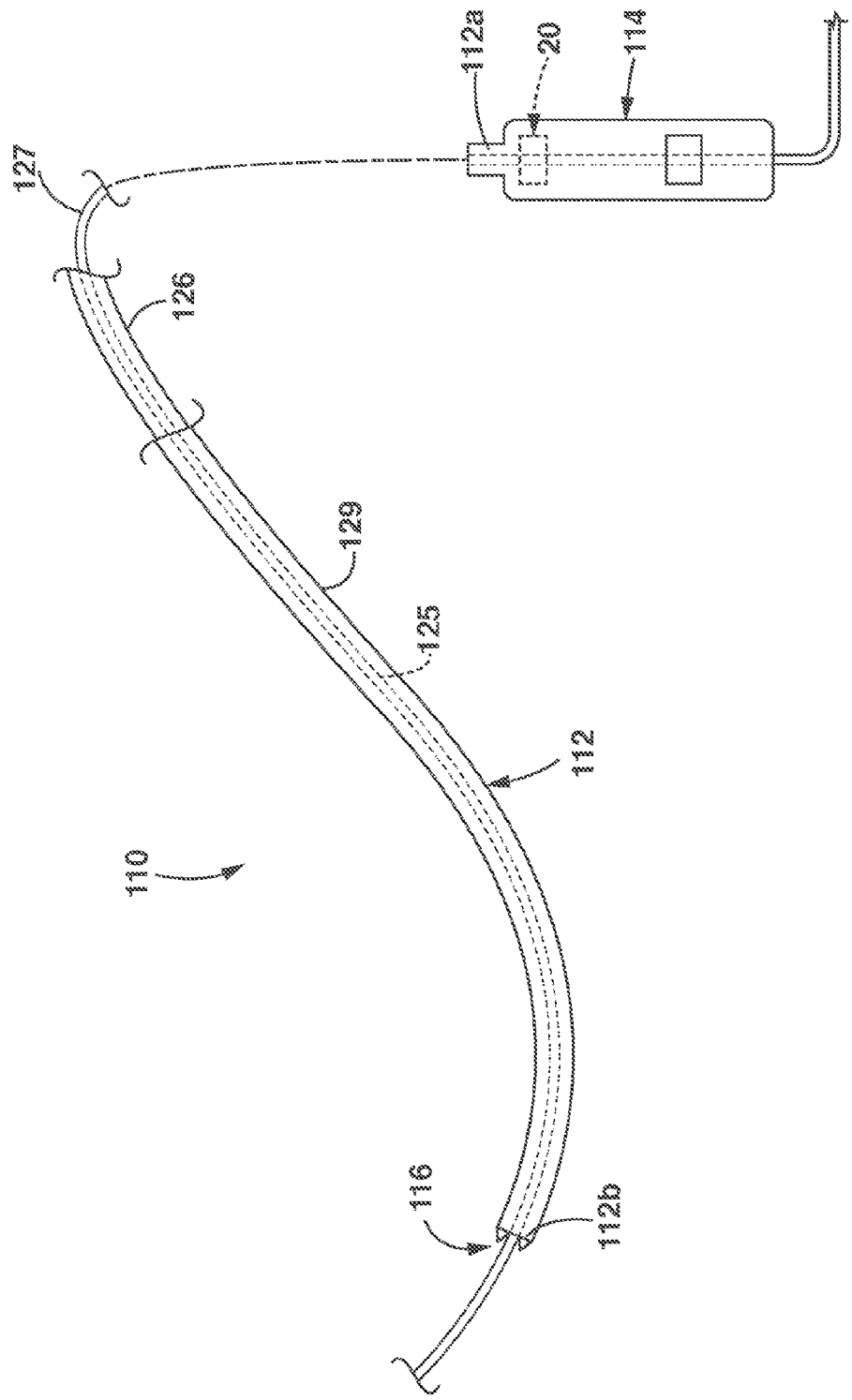
FIG. 7 is a fragmentary schematic representation of the tissue-removing catheter received on a guide wire.

Referring to FIG. 7, the illustrated drive assembly 120 is cannulated and suitable for use with another embodiment of a tissue-removing catheter, generally indicated at reference number 110. The tissue-removing catheter 110 is similar in many respects to the tissue-removing catheter 10, with corresponding parts given corresponding reference numbers plus 100. Like the catheter 10, the catheter 110 has an elongate catheter body, generally indicated at 112, extending along a longitudinal axis from a proximal end 112a to an opposite distal end 112b. Although the illustrated drive shaft 126 is received in a jacket 129, in other embodiments the catheter can include a rotatable catheter shaft that is uncovered. In the illustrated embodiment, the tissue-removing element 116 extends distally from the distal end 112b of the catheter body 112. Thus the catheter 110 is suitable for use as a crossing catheter for crossing a chronic total occlusion.

A handle or control unit, generally indicated at 114, is attachable (or attached) to the proximal end 112a of the catheter body 112 to control the catheter 110 in use. The handle 114 includes the drive assembly 20 that is operatively connected to a drive shaft 126 (broadly, a catheter shaft) and configured to selectively impart rotation and reciprocation to a tissue-removing element 116 disposed adjacent the distal end of the catheter body 112b. Unlike the catheter 10, the catheter 110 is an "on the wire" catheter, or cannulated catheter. A cannula 125 extends longitudinally through the entire catheter 110, including the tissue-removing element 116, the catheter body 112, the driveshaft 126, and, as explained in further detail below, the drive assembly 20. In FIG. 7, a guidewire 127 extends through the cannula 125. One skilled in the art will appreciate that in certain embodiments the catheter 110 can be used as a crossing catheter to form a passage through, for example, a chronic total occlusion in a body lumen to deliver the guide wire 127 through the occlusive tissue. In other embodiments, the cannula 125 allows the catheter to be properly positioned in a body lumen by threading the catheter into the body lumen over the preplaced guidewire 127. Other uses for the cannulated catheter 110 are also possible. For example, in one or more embodiments, the tissue-removing element 116 is a burr element, such as a radially expandable burr element configured to abrade tissue in the body lumen.

As shown in FIG. 6A-6D, the rotor 44, the stator 46, the drive shaft 48, and the motor 40 of the drive assembly are cannulated to define a guidewire passage 70 configured to receive the guidewire 127, as shown schematically in FIG. 7. The guidewire passage 70 is axially aligned with the cannula 125 of the catheter 110 when the handle 114 is secured to the catheter.

Figure 8:
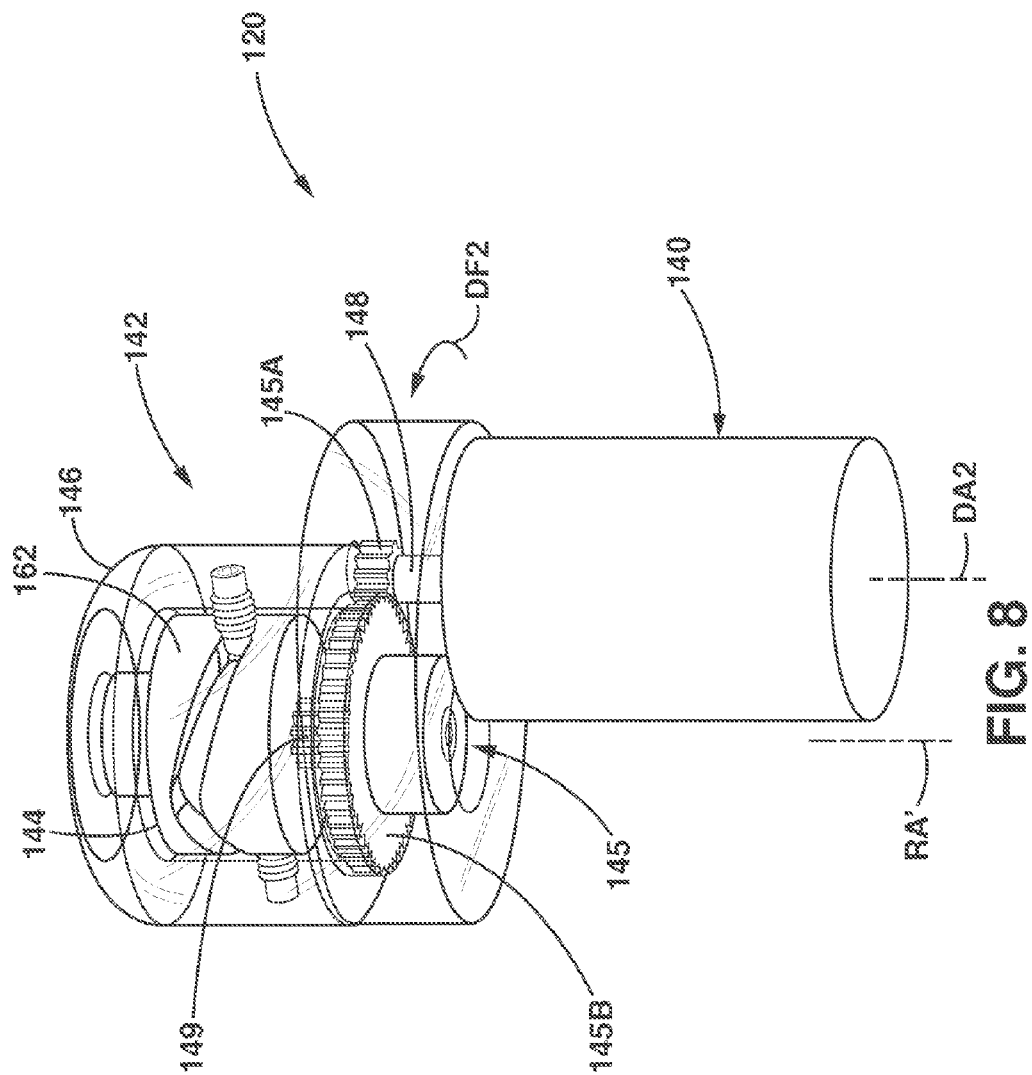
FIG. 8 is a perspective of a drive assembly of the catheter of FIG. 7, with a stator of the drive assembly illustrated as a transparent component to reveal a rotor housed within the stator.

Referring to FIG. 8, another embodiment of a cannulated drive assembly suitable for use with the catheter 110 is generally indicated at 120. Like the drive assembly 20, the cannulated drive assembly 120 includes a motor or other prime mover, generally indicated at 140, and a rotor 144 operatively connected to the drive shaft 126 and mounted on a stator 146 for rotation and reciprocation with respect to the stator relative to a rotor axis RA'. The rotor 144 and stator 146 may be substantially identical to the rotor 44 and stator 46, such that the teachings set forth above with respect to the rotor 44 and stator 46 apply equally to the present rotor 144 and stator 146, respectively.

Unlike the first drive assembly 20, the present drive assembly 120 is not direct drive. Instead, the output shaft 148 of the motor 140 is operatively connected to the rotor 144 by a drive linkage, generally indicated at 145 (broadly, a transmission mechanism). The motor 140 generates a rotational drive force DF2 about an offset drive axis DA2 that is offset from the rotor axis RA'. In the illustrated embodiment, the offset drive axis DA2 is parallel to and spaced radially apart from the rotor axis RA'. In other embodiments, the drive axis DA2 could be transverse to the rotor axis RA'. The drive linkage 145 operatively connects the motor 140 to the rotor 144 to convey the drive force DF2 and rotate the rotor about the rotor axis RA'. The rotor 144, the drive linkage 145, and the stator 146 are cannulated for the guidewire 127. Because the motor 140 is offset from the rotor axis RA', it does not interfere with the guidewire 127 extending through the drive assembly 120. Thus, the embodiment shown in FIG. 8 provides a cannulated drive assembly 120, without requiring the use of a cannulated motor 140.

Referring to FIG. 8, the drive linkage 145 is a spur gear arrangement comprising a driving gear 145A and a driven gear 145B. The driving gear 145A is operatively connected to the motor 140 for rotation about the drive axis DA2. The motor 140 is configured to impart the rotational driving force DF2 on the driving gear 145A to rotate the driving gear. The driving gear 145A is positioned in operative engagement with the driven gear 145B to impart rotation on the driven gear about the rotor axis RA'. The drive gear 145, in turn, is connected to an input shaft 149 for conjoint rotation. The input shaft 149 and the driven gear 145 are each cannulated so that the guide wire can extend through the drive assembly 120. Although the illustrated embodiment uses a spur gear arrangement, other offset drive linkages with cannulated driven links may also be used in other embodiments. When the motor 142 imparts the drive force DF2 upon the driving gear 145A, the driving gear rotates the driven gear 145B and the input shaft 149 about the rotor axis RA' to impart rotation to the rotor 144. As the rotor 144 rotates about the rotor axis RA', the rotor 144 rotates and reciprocates relative to the rotor axis RA, in the same manner as the described above with respect to the rotor 44, to ultimately impart rotation and reciprocation of the tissue removing element 116.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter configured for insertion into a body lumen of a subject, the catheter comprising:
    a drive shaft having opposite proximal and distal end portions, and a longitudinal axis extending between the proximal and distal end portions thereof;
    a tissue-removing element operatively connected to the distal end portion of the drive shaft such that rotation of the drive shaft imparts rotation of the tissue-removing element; and
    a drive assembly operatively connected to the proximal end portion of the drive shaft, the drive assembly comprising:
        a prime mover configured to generate a rotational drive force; and
        a reciprocating rotor operatively connected to the prime mover to receive the rotational drive force, the reciprocating rotor configured to simultaneously rotate about a rotor axis and reciprocate along the rotor axis in response to the rotational drive force, the reciprocating rotor being operatively connected to the proximal end portion of the drive shaft to impart rotation to the drive shaft about the longitudinal axis and reciprocation of the drive shaft along the longitudinal axis as the rotor rotates and reciprocates relative to the rotor axis;
    wherein the drive assembly further comprises a stator comprising a bearing projection configured to constrain rotation and reciprocation of the reciprocating rotor relative to the rotor axis.

2. A tissue-removing catheter as set forth in claim 1, wherein the rotor defines a race extending around the rotor axis, wherein the bearing projection is received in the race.

3. A tissue-removing catheter as set forth in claim 2, wherein the bearing projection is slidable along the race to allow rotation of the reciprocating rotor relative to the stator.

4. A tissue-removing catheter as set forth in claim 3, wherein the race is configured to allow tracking of the bearing projection therein to impart reciprocation of the rotor along the rotor axis as the rotor rotates relative to the stator.

5. A tissue-removing catheter as set forth in claim 2, wherein the race defines an axially sinuous path as the race extends only one revolution around the rotor axis.

6. A tissue-removing catheter as set forth in claim 5, wherein the race includes first and second distal apexes, the first and second distal apexes being diametrically spaced apart from one another about the rotor axis.

7. A tissue-removing catheter as set forth in claim 6, wherein the bearing projection comprises a first and second bearing projection, the first and second bearing projections being diametrically spaced apart from one another about the rotor axis.

8. A tissue-removing catheter as set forth in claim 6, wherein the race further includes third and fourth distal apexes, the third and fourth distal apexes being diametrically spaced apart from one another about the drive axis, the third and fourth distal apexes being circumferentially spaced apart from the first and second distal apexes about the rotor axis.

9. A tissue-removing catheter as set forth in claim 5 wherein the race includes at least three distal apexes that are equally circumferentially spaced about the rotor axis and the stator includes at least three bearing projections that are equally circumferentially spaced about the rotor axis.

10. A tissue-removing catheter as set forth in claim 1, wherein the stator comprises a stator housing in which the rotor is received.

11. A tissue-removing catheter as set forth in claim 10, wherein the bearing projection extends radially inward from a wall of the stator housing.

12. A tissue-removing catheter as set forth in claim 11, wherein the bearing projection comprises a bearing pin secured to the stator housing.

13. A tissue-removing catheter as set forth in claim 10, wherein the stator housing defines a distal end wall and an opening extending axially through the distal end wall in communication with the cavity, a portion of the rotor extending into the opening.

14. A tissue-removing catheter as set forth in claim 10, wherein the stator housing and the rotor are shaped and arranged to allow reciprocation of the rotor in the housing.

15. A tissue-removing catheter as set forth in claim 1, wherein the prime mover comprises an output shaft operatively connected to the rotor to transmit the rotational drive force to the rotor.

16. A tissue-removing catheter as set forth in claim 15, wherein the prime mover comprises an electric motor.

17. A tissue-removing catheter as set forth in claim 15, wherein the rotor is driven directly by the drive shaft.

18. A tissue-removing catheter as set forth in claim 17, wherein the rotor and output shaft are configured to permit reciprocation of the rotor along the rotor axis with respect to the output shaft.

19. A tissue-removing catheter as set forth in claim 15, wherein the output shaft of the prime mover is offset from the rotor axis, the drive assembly further comprising a transmission mechanism for conveying the rotational drive force from the output shaft to the rotor.

20. A tissue-removing catheter as set forth in claim 1, wherein the catheter is cannulated to define a guidewire passage configured to receive a guidewire.

21. A tissue-removing catheter configured for insertion into a body lumen of a subject, the catheter comprising:
    a drive shaft having opposite proximal and distal end portions, and a longitudinal axis extending between the proximal and distal end portions thereof;
    a tissue-removing element operatively connected to the distal end portion of the drive shaft such that rotation of the drive shaft imparts rotation of the tissue-removing element; and
    a drive assembly operatively connected to the proximal end portion of the drive shaft, the drive assembly comprising:
        a prime mover configured to generate a rotational drive force; and
        a reciprocating rotor operatively connected to the prime mover to receive the rotational drive force, the reciprocating rotor configured to simultaneously rotate about a rotor axis and reciprocate along the rotor axis in response to the rotational drive force, the reciprocating rotor being operatively connected to the proximal end portion of the drive shaft to impart rotation to the drive shaft about the longitudinal axis and reciprocation of the drive shaft along the longitudinal axis as the rotor rotates and reciprocates relative to the rotor axis;

wherein the prime mover comprises an output shaft operatively connected to the rotor to transmit the rotational drive force to the rotor; and wherein the output shaft of the prime mover is offset from the rotor axis, the drive assembly further comprising a transmission mechanism for conveying the rotational drive force from the output shaft to the rotor.

22. A tissue-removing catheter as set forth in claim 21, wherein the rotor defines a race extending a single revolution around the rotor axis and the drive assembly further comprises a stator including a portion that operatively engages the race to constrain rotation and reciprocation of the reciprocating rotor relative to the rotor axis.

23. A tissue-removing catheter as set forth in claim 22, wherein the race defines an axially sinuous path as the race extends only one revolution around the rotor axis.

24. A tissue-removing catheter as set forth in claim 23, wherein the race includes first and second distal apexes that are diametrically spaced apart from one another about the rotor axis and said portion of the stator includes first and second bearing projections that are diametrically spaced apart from one another about the rotor axis.

25. A tissue-removing catheter as set forth in claim 23, wherein the race includes at least three distal apexes that are equally circumferentially spaced about the rotor axis and said portion of the stator includes at least three bearing projections that are equally circumferentially spaced about the rotor axis.

26. A tissue-removing catheter as set forth in claim 21, wherein the catheter is cannulated to define a guidewire passage configured to receive a guidewire.

27. A tissue-removing catheter as set forth in claim 21, wherein the prime mover comprises an electric motor.

28. A tissue-removing catheter as set forth in claim 21, wherein the rotor is driven directly by the drive shaft.

29. A tissue-removing catheter as set forth in claim 28, wherein the rotor and output shaft are configured to permit reciprocation of the rotor along the rotor axis with respect to the output shaft.

* * * * *